(12) United States Patent
Luo et al.

(10) Patent No.: US 7,282,621 B2
(45) Date of Patent: Oct. 16, 2007

(54) SOMATIC RECOMBINATION

(75) Inventors: Liqun Luo, Stanford, CA (US); Hui Zong, Stanford, CA (US)

(73) Assignee: The Board of Trustees for the Leland Standford Junior University, Palo Alto, CA (US)

( * ) Notice: Subject to any disclaimer, the term of this patent is extended or adjusted under 35 U.S.C. 154(b) by 557 days.

(21) Appl. No.: 10/727,399

(22) Filed: Dec. 3, 2003

(65) Prior Publication Data

US 2005/0125850 A1     Jun. 9, 2005

(51) Int. Cl.
*A01K 67/27* (2006.01)
*C12N 15/00* (2006.01)

(52) U.S. Cl. .......................................... 800/18; 800/25
(58) Field of Classification Search ..................... None
See application file for complete search history.

(56) References Cited

OTHER PUBLICATIONS

Mao et al. (Blood 97(1):324-326, Jan. 2001).*
Kawamoto et al. (FEBS 470:263-268, 2000).*
Liu et al. (Nature Genetics 30:66-72, Jan. 2002).*

* cited by examiner

*Primary Examiner*—Valarie Bertoglio
(74) *Attorney, Agent, or Firm*—Richard Aron Osman (57) ABSTRACT

Recombination in mammalian somatic cell chromosomes is promoted and marked by a method called mosaic analysis with double marker (MADM). Mouse "knock-in" techniques are used to create pairs of chromosomes in which recombinase target sites are placed at homologous chromosomal locations. The knock-in constructs are engineered so that cellular markers, such as green or red fluorescent protein (GFP or RFP), are only expressed after recombinase-induced recombination. This system provides high-sensitivity detection of recombinase-induced mitotic recombination, even down to the single cell level. When this recombination is induced in a mouse heterozygous for a mutation in a gene distal to the "knock-in" locus on the same chromosome, it results in homozygosity of this mutation in the labeled cells. This allows the analysis in singly-labeled neurons of genes whose pleiotropic effects might otherwise result in early lethality.

10 Claims, 1 Drawing Sheet

FIG 1

SOMATIC RECOMBINATION

FIELD OF THE INVENTION

The field of the invention is generating and marking chromosome recombination in mammalian somatic cells.

BACKGROUND OF THE INVENTION

During mammalian gametogenesis homologous chromosomes in germline cells (precursors of sperm or eggs) pair and exchange genetic material through recombination. However, in somatic cells there is no significant chromosome pairing, and it is unclear whether and to what extent chromosomes can undergo recombination. If such chromosome recombination can be induced artificially, one can manipulate mammalian genomes in somatic cells and mimic many human diseases. For example, many cancers are caused by a rare event called loss of heterozygosity (LOH), during which the wild type copy of a particular gene is disrupted in an already heterozygous animal, resulting in a few homozygous mutant cells. Regulated chromosome recombination in somatic cells can mimic these situations.

We describe here the establishment in a mouse a system that allows us to generate site-directed chromosome recombination in somatic cells. An important added advantage of our system is the ability to label only those homozygous mutant cells in an otherwise heterozygous and hence genetically mosaic animal. Such manipulations may also be used not only to create mouse models for various human diseases, but also to study gene function in particular tissues and developmental stages, and to provide high-resolution anatomical analysis of pathology resulting from gene mutations.

SUMMARY OF THE INVENTION

The invention provides a general method to generate and mark chromosome recombination in mammalian somatic cells; in particular embodiments, we call this method mosaic analysis with double marker (MADM).

The disclosed system labels particular cells to reveal their detailed morphology and function while simultaneously modifying target genes-of-interest only in these labeled cells. For example, particular labeled neurons in the brain reveal detailed axon/dendrite morphology associated with a modification to a target gene. In one embodiment of the invention, mouse "knock-in" techniques are used to create pairs of chromosomes in which recombinase target sites, such as the DNA target for Cre recombinase, are placed at homologous chromosomal locations. The knock-in constructs are engineered so that cellular markers, such as green or red fluorescent protein (GFP or RFP), are only expressed after recombinase-induced recombination. Thus, this system allows for high-sensitivity detection of recombinase-induced recombination, even down to the single cell level. When this recombination is induced in a mouse heterozygous for a mutation in a gene distal to the "knock-in" locus on the same chromosome, it results in homozygosity of this mutation in the labeled cells. This allows the analysis in singly-labeled neurons of genes whose pleiotropic effects might otherwise result in early lethality. Of course, neuronal analysis is exemplary and this method can equally analyze gene function outside the nervous system.

The invention provides, inter alia, 1) the first demonstration that recombination between homologous chromosomes can be generated with useful frequency in somatic cells of living mice; 2) the first demonstration that some of the chromosome exchanges above could result in mosaic animals with homozygous mutant cells in an otherwise heterozygous animal; and 3) unique labeling of isolated cells of heterozyous genotype (G1, or G2/Z) or of homozygous genotypes (G2/X). In addition to marking mitotic recombinations, the invention also provides marking of post-mitotic recombinations, which are double colored just as G2/Z and G1 recombinations, clearly distinguishable from G2/X recombinations, and can be used for conditional knock-outs made by introducing candidate mutant genes. Prior to our disclosure, there was no rational or reasonable expectation that somatic recombination could be induced or detected at a measurable or useful frequency in mammals or mice in particular, wherein unlike fly chromosomes which pair in mitosis, mouse chromosomes do not.

Accordingly, in one embodiment, the invention provides a transgenic mouse comprising genomic somatic cells and recombined somatic cells comprising a recombinase-induced, somatically recombined chromosome pair, wherein the genomic cells comprise:

(a) a first recombinase target site in a first chromosome of a chromosome pair;

(b) a second recombinase target site at a homologous location of a second chromosome of the chromosome pair;

(c) a recombinase functionally expressed by the genomic cells, and which promotes recombination between the target sites of the first and second chromosomes;

wherein recombinase-promoted somatic mitotic recombination between the target sites yields the somatically recombined chromosome pair of the recombined somatic cells.

This embodiment is amenable to any method-compatible labeling system, including wherein the chomosome pair further comprises a single-signal MARCM-type labeling system, as described below, or wherein the chromosome pair further comprises a dual-signal MADM-type labeling system, as described below.

In more particular embodiments, the mouse is determined to have a somatic recombination frequency of between $10^{-2}$ and $10^{-6}$. Recombination frequency may be modulated by a variety of protocols, including recombinase promoter selection and activation (further described below). Depending on the application, target recombination frequency ranges may be in the higher (e.g. $10^{-2}$ to $10^{-3}$, $10^{-3}$ to $10^{-4}$, etc.) or lower (e.g. $10^{-4}$ to $10^{-5}$, $10^{-5}$ to $10^{-6}$, etc.) ranges of those empirically obtainable.

In other embodiments, the invention provides methods of making and using such mice. For example, the invention provides a method to generate chromosome recombination in somatic cells in a subject mouse, such as described above, the method comprising the steps of:

(a) introducing in a first chromosome of a chromosome pair of a pluripotent cell, a first recombinase target site;

(b) introducing at a homologous location of a second chromosome of the chromosome pair of the pluripotent cell, a second recombinase target site;

wherein the cell encodes a recombinase which promotes recombination between the target sites of the first and second chromosomes; and (c) growing the cell to obtain a mouse comprising differentiated progeny cells of the pluripotent cell, wherein recombinase-induced somatic mitotic recombination between the target sites yields the somatically recombined chromosome pair of the recombined somatic cells.

As above, these methods are amenable to any method-compatible labeling system, including wherein the chromosome pair further comprises a single-signal MARCM-type labeling system, as described below, or wherein the chromosome pair further comprises a dual-signal MADM-type labeling system, as described below.

In more particular embodiments, the mouse is determined to have a somatic recombination frequency of between $10^{-2}$ and $10^{-6}$. Recombination frequency may be modulated by a variety of protocols, including recombinase promoter selection and activation (further described below). Depending on the application, target recombination frequency ranges may be in the higher (e.g. $10^{-2}$ to $10^{-3}$, $10^{-3}$ to $10^{-4}$, etc.) or lower (e.g. $10^{-4}$ to $10^{-5}$, $10^{-5}$ to $10^{-6}$, etc.) ranges of those empirically obtainable. Accordingly, the method may be practiced wherein the method further comprises the step of:

(d) detecting in the mouse a particular somatic recombination frequency, such as between $10^{-2}$ and $10^{-6}$.

In another embodiment, the invention provides a transgenic mouse comprising a somatic cell, comprising:

(a) in a first chromosome of a chromosome pair, a polynucleotide comprising a promoter operably linked to a chimeric sequence encoding an N-terminal portion of a first marker and a C-terminal portion of a second marker separated by a recombinase target site;

(b) at a homologous location of a second chromosome of the chromosome pair, a polynucleotide comprising a promoter operably linked to a chimeric sequence encoding an N-terminal portion of the second marker and a C-terminal portion of the first marker separated by a reconabinase target site; and (c) a recombinase expressed by the cell, and which promotes recombination between the target sites of the first and second chromosomes;

wherein recombinase-promoted somatic mitotic recombination between the target sites yields alternative pairs of X- or Z-segregated progeny cells, wherein the X-segregated progeny cells comprise a first progeny cell comprising the first chromosome, and a recombined variant of the second chromosome comprising the promoter operably linked to a sequence encoding the N- and C-terminal portions of the second marker; and a second progeny cell comprising the second chromosome, and a recombined variant of the first chromosome comprising the promoter operably linked to a sequence encoding the N- and C-terminal portions of the first marker, and wherein the Z-segregated progeny cells comprise a first progeny cell comprising the first chromosome and the second chromosome, and a second progeny cell comprising a recombined variant of the first chromosome comprising the promoter operably linked to a sequence encoding the N- and C-terminal portions of the first marker; and a recombined variant of the second chromosome comprising the promoter operably linked to a sequence encoding the N- and C-terminal portions of the second marker, wherein the first X-segregated progeny cell produces a second marker-specific signal, the second X-segregated progeny cell produces a first marker-specific signal, the first Z-segregated progeny cell produces neither a first nor second marker-specific signal, and the second Z-segregated progeny cell produces both a first and a second marker specific-signal.

In another embodiment, the invention provides a method to generate and mark chromosome recombination in somatic cells in a subject mouse by:

(a) introducing in a first chromosome of a chromosome pair of a pluripotent cell, a polynucleotide comprising a promoter operably linked to a chimeric sequence encoding an N-terminal portion of a first marker and a C-terminal portion of a second marker separated by a recombinase target site;

(b) introducing at a homologous location of a second chromosome of the chromosome pair of the pluripotent cell, a polynucleotide comprising a promoter operably linked to a chimeric sequence encoding an N-terminal portion of the second marker and a C-terminal portion of the first marker separated by a recombinase target site, wherein the cell expresses a recombinase which promotes recombination between the target sites of the first and second chromosomes; and (c) growing the cell to obtain a mouse comprising differentiated progeny cells of the pluripotent cell, wherein recombinase-promoted somatic mitotic recombination between the target sites in a differentiated progeny cell yields alternative pairs of X- or Z-segregated progeny cells, wherein the X-segregated progeny cells comprise a first progeny cell comprising the first chromosome, and a recombined variant of the second chromosome comprising the promoter operably linked to a sequence encoding the N- and C-terminal portions of the second marker; and a second progeny cell comprising the second chromosome, and a recombined variant of the first chromosome comprising the promoter operably linked to a sequence encoding the N- and C-terminal portions of the first marker, and wherein the Z-segregated progeny cells comprise a first progeny cell comprising the first chromosome and the second chromosome, and a second progeny cell comprising a recombined variant of the first chromosome comprising the promoter operably linked to a sequence encoding the N- and C-terminal portions of the first marker; and a recombined variant of the second chromosome comprising the promoter operably linked to a sequence encoding the N- and C-terminal portions of the second marker, wherein the first X-segregated progeny cell produces a second marker-specific signal, the second X-segregated progeny cell produces a first marker-specific signal, the first Z-segregated progeny cell produces neither a first nor second marker-specific signal, and the second Z-segregated progeny cell produces both a first and a second marker specific-signal.

In another embodiment, the invention provides a method to generate and mark chromosome recombination in somatic cells in a subject mouse by:

(a) introducing in a first chromosome of a chromosome pair of a pluripotent cell, a polynucleotide comprising a promoter operably linked to a chimeric sequence encoding an N-terminal portion of a first marker and a C-terminal portion of a second marker separated by a recombinase target site;

(b) introducing at a homologous location of a second chromosome of the chromosome pair of the pluripotent cell, a polynucleotide comprising a promoter operably linked to a chimeric sequence encoding an N-terminal portion of the second marker and a C-terminal portion of the first marker separated by a recombinase target site, wherein the cell expresses a recombinase which promotes recombination between the target sites of the first and second chromosomes; and (c) growing the cell to obtain a mouse comprising differentiated progeny cells of the pluripotent cell, wherein recombinase-promoted somatic recombination between the target sites in a differentiated progeny cell yields a recombined cell comprising a recombined variant of the first chromosome comprising the promoter operably linked to a sequence encoding the N- and C-terminal portions of the first marker; and a recombined variant of the second chromosome comprising the promoter operably linked to a sequence encoding the N- and C-terminal portions of the second marker, wherein the recombined cell produces both a first and a second marker specific-signal.

The recited recombinase refers to any recombinase which catalyzes a site-specific recombination at a corresponding target site. Suitable recombinases include, for example, Cre recombinase (Sauer et al. (1993) Methods in Enzymology 225: 898) and Flp recombinase (Buchholz et al. (1996) Nucl. Acids Res. 24:4256-4262; Buchholz et al. (1998) Nat. Biotechnol. 16:657-662). For example, in many embodiments, the Cre/LoxP system is interchangeable with the FRT/FLP system, which has also been demonstrated to work in mice. Other recombinases which may be adapted to our system include Rs, RAG1/2, etc. In addition, alternative recombinases with novel specificity may be generated using established mutation and selection protocols, e.g. Buchholz et al., Nat Biotechnol. 2001 Nov.; 19(11):1047-52.

Depending on the application, the recombinase may be selected or engineered to be expressed in restricted cell types. A wide range of promoters is well known in the art to provide tissue or cell-type or developmental-stage specific expression, and hence target or restrict recombinase expression to a predetermined developmental stage or cell or tissue type. In addition, functional expression of the recombinase may be temporally restricted by requiring exogenous activation. A wide variety of techniques are known in the art for selective activation of target genes at the level of both transcriptional activation and protein activation. For example, drug-induced promoters (e.g. tamoxifen- or doxycycline-inducible promoters) may be used to activate recombinase expression by administration of the corresponding drug. Alternatively, the recombinase may be expressed in an inactive or pro form subsequently activated, directly or indirectly, with a specific inducer, as described for example, in Dueber et al., 2003 Science 301, 1904-8.

These protocols for controlling recombinase expression also provide venues for regulating recombination frequency; for example, by limiting the amount of inducer administered to an animal wherein functional recombinase expression is regulated by the inducer, e.g an inducer activated promoter, or an inducer-activated recombinase or indirectly activating enzyme. For example, in particular embodiments, it is desirable to limit recombination frequency, for example, to more easily resolve densely packed cells, or cells with complex morphology such as neurons with large dendritic trees and/or long axons.

The recited recombinase target site refers to a nucleotide sequence which undergoes recombination (e.g., DNA crossover and exchange) when catalyzed by a recombinase, such as Cre, Flp or another member of the Int family of recombinases (Argos et al. (1986) EMBO J. 5: 433). Suitable target sequences include, for example, the lox sequences recognized by Cre recombinase, and the frt sequences recognized by Flp recombinase.

The recited first and second markers may be any proteins providing directly, indirectly or inferentially detectable and distinguishable signals and that are otherwise compatible with the recited cells, animals and methods, e.g. they are not cytotoxic. Exemplary markers include fluorescent proteins like GFP, RFP, phycobiliproteins, etc.; chromogenic proteins that catalyze a chromogenic reaction, such as bacterial β-galactosidase, placenta alkaline phosphatase, luciferase, etc.; proteins providing a specific binding target of a detection reagent, such as a homologous or heterologous epitope targetable by a specific antibody detection reagent, such as a HIS-tag, etc; proteins that provide a physiological readout, such as a change in $Ca^{++}$, pH, etc., or other parameter of cell function, including viability; proteins that provide a transcriptional readout, such as transcriptional regulators, activators, or inhibitors, such as Gal4, etc; and etc.

The recited pluripotent cell encompasses cells which are capable of developing into the recited mammal, typically ES cells or fertilized egg cells.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

Depending on when recombination happens during the cell cycle, chromosome exchange in somatic cells can have different outcomes. When chromosome exchange happens at G1 phase of a proliferating cell, or in post-mitotic cells (G1 recombination), the exchange of chromosomes does not result in a change of genetic materials in that cell or its progeny. When chromosome exchange happens at G2 phase of a proliferating cell (mitotic recombination), there are two distinct segregation patterns. If the recombined chromotids go into the same daughter cell (G2-Z segregation), again there is no net change of genetic information. However, if after G2 recombination, the recombined sister chromotids are segregated into two daughter cells (G2-X segregation), then each daughter cell is homozygous for the part of the chromosome that is distal to the recombination site. If the mouse has a mutated gene located in that portion of one of the chromosomes, then one of the daughter cells (and all its descendants) will become homozygous mutant for that gene after such a "mitotic recombination" event. Thus chromosome exchanges at G2 phase of the cell cycle could be used to generate mosaic animals in which only a small subset of cells are homozygous mutant. However in order to make use of this property, it is essential to mark these events specifically, and to distinguish G2-X from G1 and G2-Z recombinations, as only G2-X is capable of generating genetic mosaic animals.

We used the mouse "knock-in" technique to create pairs of chromosomes in which loxP sites, the cis element for Cre-mediated recombination, are placed at homologous chromosome locations. The key design is to create chimeric GFP (EGFP) and RFP (DsRed2) proteins, N-GFP::C-RFP and N-RFP::C-GFP (see FIG. 1; referred to herein as G-R and R-G). They are under the control of a strong and ubiquitous promoter that allows high-level expression in all cells. However, these chimeric proteins are colorless since each contains only part of the protein and GFP and RFP share only limited homology. As an added precaution, we created a frame shift at the fusion site of the chimeric proteins such that the carboxyl half of the protein is out of the reading frame, to ensure that no color can be generated from these chimeric proteins. An intron containing a loxP site has been inserted between the GFP and RFP portions of the chimeric proteins. This pair of loxP sites directs recombination in the presence of the Cre recombinase, but does not interfere with protein translation since it is removed after mRNA splicing. In this design, G1 and G2-Z recombination will be double-labeled with green and red, whereas G2-X recombination will result in singly labeled cells, with green cells being siblings of red cells. If a mutation is introduced distal to the R-G knock-in cassette, for instance, then green cells will be homozygous mutant, red will be homozygous wild-type, and all unlabeled or double-labeled cells will be heterozygous.

We have generated the G-R and R-G knock-in mouse lines via homologous recombination in ES cells. We have crossed these mice with an actin-Cre mouse line in which Cre is expressed ubiquitously, or K5-Cre in which Cre is expressed in skin precursor cells, or BF 1-Cre in which Cre is expressed in forebrain precursor cells. Only when mice carried all three elements (G-R knock-in, R-G knock-in and Cre) did we observe labeled cells. We have observed both double-labeled cells and red-only or green-only cells. The red-only and green-only cells are usually close by each other, consistent with they being the product of mitotic recombination. We have observed these events in all tissues we have analyzed (brain, retina, skin, heart, liver, skeletal muscle, etc.) although the frequency varies as a result of different expression levels of the Cre recombinase in different tissues. Thus, we have demonstrated that 1) exchange of homologous chromosomes can occur at high frequency in mammalian somatic cells using Cre/LoxP mediated interchromosomal recombination; 2) some of the recombination events are due to G2/X segregation during mitosis, and therefore can be used as a general method for conditionally deleting a gene from specifically labeled cells; 3) different recombination events can be unequivocally distinguished with our double marker system.

The first usage of our system is to generate conditional knock-out mice—deleting genes with temporal and spatial precision. The existing conditional knock-out method inserts two LoxP sites flanking a portion of the gene of interest. Then such mice are crossed with transgenic mice carrying a temporal and/or spatial restricted Cre to generate "conditional knock-outs". There are several advantages of our method over prior methods, including:

1) Using our method, we can place the set of knock-in constructs at the centrosomal side of each chromosome in the mouse. Each pair then can be used for conditionally knocking out any gene that is distal to that loxP site. Therefore the system can be used for systematically generating conditional knock-out mice, rather than the current method of doing one gene at a time, providing long-term gains in efficiency and cost-effectiveness.

2) The existing method is restricted to the analysis of mutations that are made through gene targeting. Our method can also be used to analyze naturally occurring mutants. In addition, it can also be used to screen for chemically mutagenized chromosomes to identify new genes, whose homozygosity in a subset of identified cells would lead to a phenotype of interest.

3) Another important advantage of our system over existing conditional knock out systems is our ability to uniquely mark homozygous mutant cells, and in fact their wild-type siblings with a different color in the same animal. This greatly facilitates the analysis of the consequence of gene knock out to the cells and tissues of interest. The existing conditional knock-out method does not mark the cells that are homozygous mutant for the gene of interest. Even if one engineers a marker after the second LoxP site, which for most of the genes are not feasible due to the technical difficulties, these mutant cells may not be stably marked because the promoter activation may not persist. In our system the marker is typically under the control of a ubiquitous promoter that stays on. Given the longer life span of mice and often the need to analyze gene function weeks to months after the recombination event, a stable marking system for the mutant cells is a great advantage. Also because the efficiency of mitotic recombination is not very high, labeled mutant cells in our system can be individually identified allowing high resolution anatomical analysis. This latter property is especially important for analyzing gene function in the nervous system, or for analyzing animal models of neurological diseases. The ability to trace dendritic trees and axon projection of individual neurons is essential for studying normal biology and analyzing pathological phenotypes.

In addition to conditional knock out of genes, our system offers an efficient way to label individual cells (without introducing mutants) to analyze normal development (for instance lineage tracing) or if introduced into a whole animal mutant background (such as a mouse model for human disease) to provide high resolution morphological analysis. Our system can also be easily adapted to other genetic manipulations in mice, such as expressing a wild-type or mutant transgene only in a small subset of identifiable neurons (below), which can be used to mimic activation (dominant) mutations in numerous human diseases.

For example, sometimes it is desirable to express a transgene in a small population of labeled cells, to mimic for instance the activation of an oncogenic mutation and follow the tumor growth. Our system can be easily adapted to achieve that. For instance, the RFP portion of the design could be replaced with a transcription factor such as GAL4, such that only after chromosomal recombination will a functional GAL4 be restored. GAL4 can then direct expression of not only a second marker, but also any other gene under the control of GAL4-UAS (upstream activating sequence), demonstrated to work in many organisms including mice. In this case, G1, G2-Z and G2-X events are all useful.

EXAMPLES

Single Neuron Labeling and Genetic Manipulation in Mice

Much of our current understanding of the neuronal structure, connection, development and organization derive from Ramon y Cajal's systematic studies using the Golgi method [1]. Golgi staining method randomly labels a very small population of neurons in their entirety, allowing for detailed visualization of the elaborate dendritic trees and extensive axonal projections of individual neurons. Another important technique that has contributed to the advancement of modern neurobiology is the genetic manipulation method, known as "gene targeting" or "knockout" technique in mice.

Through homologous recombination, a single endogenous gene can be selectively targeted for removal [2]. Taking advantage of this technique, many genes have been removed genetically and the loss-of-function phenotype analyzed to implicate their roles in neuronal development. Though powerful, gene targeting has one major caveat: most genes have pleiotropic functions so that their removal will lead to early embryonic lethality in mice, impeding the analysis of the functions of these genes in neuronal development. To circumvent this obstacle, a technique called "conditional knockout" emerged. Using Cre-loxP-directed recombination, genes can be removed with temporal or spatial control by restricting Cre recombinase expression to particular developmental stages or a subset of tissues [3].

However, due to the highly migratory nature of developing neurons (e.g. cortex layer development), it is difficult to trace mutant neurons after they are generated. While GFP replacement knockout or secondary marker methods have been utilized to label mutant neurons, it is still difficult to study the detailed structural defects of these "knockout" neurons for two reasons: 1) too many mutant neurons are generated, which causes a low resolution due to the intertwining nature of axons and dendrites; 2) In the case of GFP replacement knockout, the endogenous gene promoters often fail to express high enough levels of GFP for the sensitive detection. In later stages of development or in the adult animal, GFP detection will be even harder because endogenous promoters usually attenuate, sometimes even turn off their transcription machinery after early development.

A system that combines the assets of the Golgi method with the strength of precise genetic manipulation in mice would be ideal to examine gene function in neural network development and function. Our mouse MADM system is designed to fit this need. It enables us to generate singly-labeled neurons, and knock out a gene-of-interest only in these neurons. This system offers important advantages including: 1) the functions of genes can be assessed in a single clearly labeled neuron, increasing the power of phenotypic detection; 2) gene function can be tested in the tissue and developmental stages of interest without being confounded by the gene's pleiotropic effects; and 3) cell-autonomy of gene action can be determined. Additionally, due to its use of mitotic events, this system is an ideal tool to trace neuronal lineage (including adult neural stem cells) and discern the logic of neural circuit assembly. Our previously reported *Drosophila*-based system has proven very fruitful in these aspects [4, 5].

Our MADM system generates homozygous mutant cells expressing unique color markers via a site-directed mitotic recombination event. The key design of this scheme is to create chimeric GFP and RFP proteins, N-GFP::C-RFP and N-RFP::C-GFP (see FIG. 1, part A, also referred to as GR and RG). The chimeric proteins will be colorless due to a frame shift at the fusion site that puts the carboxyl half in a different reading frame from the N-terminal half. An intron containing a loxP site is inserted between the GFP and RFP portions of the chimeric constructs. This pair of loxP sites serves as the cis element to direct recombination induced by Cre recombinase, but does not interfere with protein translation since it will be removed by mRNA splicing.

Figure 1:
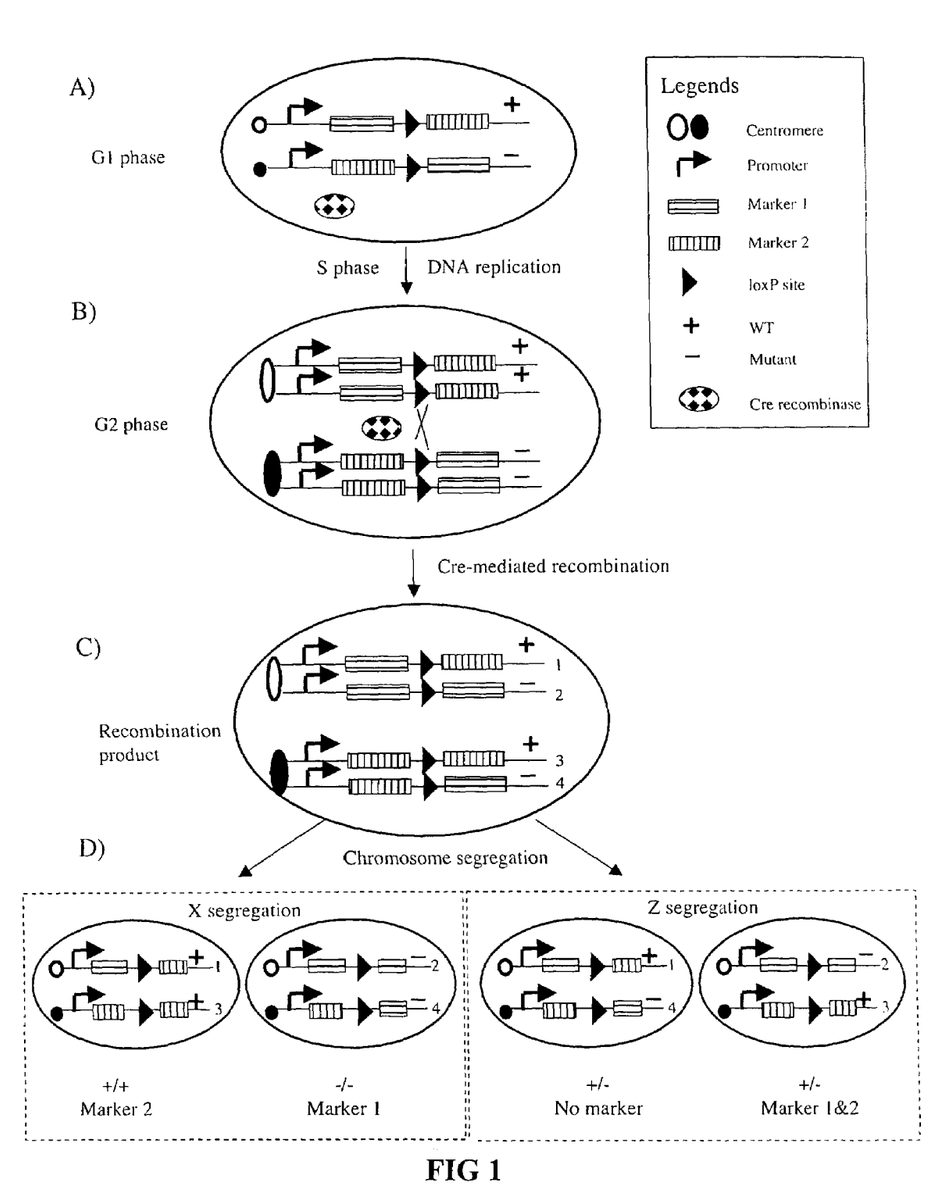
FIG. 1. Exemplary MADM scheme for double-color labeling of somatic recombination.

The MADM system requires two knock-in mouse lines—one carrying the GR and the other the RG expression cassette. These mouse lines will be crossed with appropriate Cre mice and their progeny will be mated with each other to generate mice carrying 1) GR, 2) RG; 3) Cre recombinase. In proliferating cells after DNA replication (at G2 phase), the Cre enzyme will induce recombination between loxP sites on two homologous chromosomes (FIG. 1, part B). As a consequence of this mitotic recombination, functional GFP- and RFP-expression cassettes will be restored (FIG. 1, part C). If this recombination occurs in mice heterozygous for a mutant gene that is located distally to the knock-in site, there would be two possible types of segregation during mitosis (FIG. 1, part D). X segregation (segregation of two recombinant sister chromatids, usually more prevalent) will produce two daughter cells—one red cell that is homozygous wild type, and one green cell that is homozygous mutant. This highlights another advantage of our double-color labeling scheme: the simultaneous labeling of both daughter cells, allowing side by side comparison of the wild-type cell and the homozygous mutant cell (and their progeny if neural precursors are targeted). Z segregation (two recombinant sister chromatids go into the same daughter cell), on the other hand, will generate two heterozygous cells—one has no color and another has both red and green colors. Even if both segregation events happen at different cell divisions in the same animal, we will be able to distinguish between these two modes of segregation, and unequivocally identify which labeled neurons are mutant.

Construction of expression cassette and GFP—RFP chimeras. First, a loxP site was inserted into the β-globin intron, which was then inserted into the open reading frame of GFP and RFP. A unique restriction site was also introduced near the loxP site for generating chimeric proteins. The efficiency of the splicing has been confirmed by Western blots following COS cell transfection of these intron containing constructs.

Second, a pCA vector was constructed to express our proteins. This expression cassette contains a CMV β-actin enhancer-promoter (CA promoter) [6] and the SV40 T antigen polyA signal that allows for ubiquitous and high-level expression. The vector was tested in both COS cells and neurons in brain slices. P8 rat hippocampal slices were cultured and then transfected with pCA-GFP or pCA-RFP constructs using biolistic method [7]. The fluorescent proteins were well expressed in both astrocytes and pyramidal neurons. Both markers label axons and the entire dendritic trees including dendritic spines. The efficiency of splicing was also confirmed with this assay.

Finally, GR and RG chimeras were constructed, and the functional restoration of GFP/RFP was verified by co-transfecting GR, RG and a Cre-expressing construct in hippocampal slices. Having validated the chimeric marker approach, a loxP-flanked $Neo^r$ gene was inserted into the intron for positive selection of knock-in events in ES cells.

Mouse knock-in to generate GR and RG mice. These experiments demonstrate that the MADM technique will generate RG and GR insertions on the long arm of chromosome 6. The chromosome locus used for the "knock-in" is ROSA26[8], which locus is well characterized and allows high-level ubiquitous expression of the inserted gene, starting at the morula-blastocyst stage [9]. Therefore, we can examine the efficiency of mitotic recombination events in the whole animal without concern for the spatial and temporal restrictions or silencing effects of local chromatin structure. Additionally, mice homozygous for ROSA26 targeted insertions do not exhibit detectable phenotypes [9]. This is important because our strategy has knock-in cassettes at this locus on both homologous chromosomes.

We have demonstrated successful germline transmission in GR, RG and GFP knock-in mice. The GFP mouse serves as a control for the expression level driven by the CA promoter at ROSA26 locus, wherein GFP is expressed in all stages (from embryo to adult) in the brain.

Cross with Cre mice to demonstrate the proof-of-principle. GR and RG mice are crossed with the β-actin-Cre mice (ubiquitous Cre expression) [10] to obtain GR;Cre mice and RG;Cre mice, respectively. Then these two mouse lines are crossed with each other to obtain GR/RG;Cre mice. The brains of these mice are examined for green, red or double-labeled cells during different developmental stages to confirm essential parameters of our system: 1) the efficiency of recombination, reflected by the numbers of colored cells; 2) the frequency of G2 recombination followed by X segregation (the informative segregation pattern) by comparing the number of single-colored cells vs. double-colored cells; 3) lineage relationship, i.e. whether labeled neurons are close to each other, what is the clone size; 4) detection sensitivity, i.e. expression level of GFP, RFP; 5) resolution of the detailed structure of labeled neurons, e.g. fine axon processes, dendritic spines, etc.

Functional testing of candidate genes in neuronal development. Among genes distal to ROSA26 on mouse chromosome 6 are K-Ras and Raf-1, both of which have been knocked out by standard gene targeting [11, 12]. Neuronal defects have not been closely examined because both mutants are embryonically lethal [11, 12]. Ras and Raf are key intracellular signaling molecules that mediate the action of a variety of extracellular signals important for neuronal differentiation, plasticity and survival [for reviews, see 13, 14]. We use our MADM technology to generate labeled, homozygous mutant neurons in otherwise heterozygous brains, and study the consequence of loss of Ras or Raf on neuron morphology and physiology.

K-Ras and Raf-1 heterozygous knockout mice are obtained and crossed with RG mice, and then screened for recombinants (e.g. RG,K-Ras$^-$/+). This strain is then crossed with homozygous GR;Cre mice. The resulting RG,K-Ras$^-$/GR;Cre mice have a mosaic brain with homozygous mutant cells expressing GFP, and wild type sibling cells expressing RFP. The morphological development of these neurons are assayed in well-defined brain regions (such as cerebellar Purkinje cells) and the physiological properties (such as cerebellar LTD) of these mutant neurons are studied using electrophysiology in brain slices.

Circuit tracing of mitral cell projection to the olfactory cortex. Olfactory receptor neurons that express the same receptor converge their axons onto a common glomerulus, creating an odor map in the olfactory bulb or insect equivalent. Mitral/tufted cells (projection neurons in insects) then relay the information from glomeruli to higher olfactory centers by sending dendrites to a single glomerulus and axons to the olfactory cortex. How odor is represented beyond the olfactory bulb is largely unknown. A recent trans-neuronal labeling study using wheat germ agglutinin (WGA) begins to address this question [15], however expanding these studies to more classes of neurons would be labor-intensive and does not provide high anatomical resolution.

Using the *Drosophila* MARCM (mosaic analysis with repressible marker) system, a predecessor to mouse MADM, our lab found that projection neurons (PNs) are pre-specified by birth order to send dendrites to specific glomeruli and therefore carry specific olfactory information [16]. Furthermore, we demonstrated that each PN has distinct, stereotyped axon branching patterns and terminal fields in the higher olfactory centers, determined by which glomerulus it innervates. This map is characterized by spatial convergence and divergence of PN axons [17, 18]. Our findings indicate that projection neurons could relay information from specific glomeruli to higher olfactory centers with their stereotyped axonal projections. Thus, specific odorants could activate stereotyped sets of third order neurons in the higher centers, which could then release specific innate olfactory-mediated behavior.

The MADM system allows us to perform analogous experiments in mice to test to what extent the principles we found in *Drosophila* apply to the mammalian brain. Using a Cre line that is expressed in mitral cell precursors [19], we can study mitral cell lineage and systematically trace their axon projections in different parts of the olfactory cortex correlating with their glomerular locations.

An important advantage of using our method to trace circuits (as compared to Golgi staining, for instance) is the ability to restrict labeling to a specific class of neurons, provided cell-type specific Cre mice can be obtained. More elegantly, using inducible Cre (e.g. Tet-off, tamoxifen) to restrict the developmental time window for mitotic recombination, we are able to target a particular class of neurons based on their specific time of neurogenesis. In addition, the ability to couple the labeling with homozygous deletion of candidate genes allows us to study the molecular mechanisms of neural circuit assembly.

Inter-chromosomal recombination efficiency during mitosis. Several studies have shown that the efficiency of Cre-loxP mediated translocation between non-homologous chromosomes in embryonic stem (ES) cells is about $10^{-7}$ to $10^{-4}$ [20-23]. However, a recent study demonstrated that recombination between homologous sites on homologous chromosomes, had an increased efficiency of $10^{-4}$~$5 \times 10^{-2}$ in ES cells, varying between different chromosomal loci [24]. Using a different methodology, an independent study reported a $10^{-4}$ inter-chromosomal recombination efficiency for mouse chromosome 1 [25]. The mouse brain is estimated to have $10^9$ neurons. We find that the rate of homologous recombination in neural precursor cells is comparable to that in ES cells, generating $10^5$ to $5 \times 10^7$ labeled neurons per brain using a ubiquitous Cre line. Hence, our method is highly efficient in generating labeled clones. Where a particular application imposes recombination rates too high to allow generation and visualization of well-isolated neuron clones, the rate can be limited by reducing the expression level of Cre, or controlling Cre expression spatially and/or temporally.

G1 recombination and G2 recombination followed by Z segregation. For mutant analysis, only G2 recombination followed by X segregation (FIG. 1, part D) will be informative; it will generate one green daughter cell (and all its subsequent progeny) that is homozygous mutant, and one red daughter (and all its subsequent progeny) which is homozygous wild type. However, G2 recombination followed by Z segregation or G1 recombination can also occur, which would generate double-colored heterozygous cells that are less informative. Our double-color system was designed to unequivocally distinguish G2-X from G2-Z or G1 recombination events. Liu et al. showed that in all recombination events in ES cells, G2/X occurs at the frequency of 60-100%, depending on the loci, while G1 or G2/Z events (cannot be distinguished in their studies) account for 0-40% [24]. Therefore, more than half of the recombination events should be informative for our purpose. Finally, for systematically tracing neuronal projections or for lineage analysis (in which no mutant is introduced), all recombination events are informative.

We have established our knock-in recombination system and shown its utility for detailed phenotypic analysis. We have also demonstrated the invention to generate mice models of human diseases, including modeling mutations in tumor suppressor genes. By creating a set of knock-in mice at the centromeric end of every mouse chromosome arm, essentially all mouse genes can be examined using this method. Our MADM system offers a unique opportunity to study many biological problems at a single-cell resolution, and provides insight into many complex systems, especially the function of mammalian brains.

Different tissue-specific Cre lines are being rapidly established, constantly expanding our tools to systematically study the assembly of neural circuits. Using these Cre mice, the MADM system permits tracing complex neural circuits throughout the mouse brain [analogous to 16, 17]. Our system also provides a powerful tool to analyze gene function in defined neural circuits. For example, a loxP-containing chromosome can also be recombined with any mutant (knockout or naturally occurring) on that chromosome arm for mosaic analysis—generating green homologous mutant neurons in a heterozygous animal. The roles of these genes in neuron development can be studied at a whole new level of resolution. Furthermore, the clearly labeled wild type or mutant neurons can be used in electrophysiological recording or optical imaging in brain slices or in the intact animal to reveal the roles of this particular gene in neural circuit function. Furthermore, our MADM system does not have to be limited to the distal side of the targeting chromosome. In dominant mutant or homozygous mutant animals that are viable but have neuronal defects, our system can be utilized as a labeling tool to characterize the neuronal phenotype with single-cell resolution. The system can also be expanded by replacing GFP with other markers, such as genetically encoded $Ca^{++}$ indicators or voltage indicators. With this type of modification, physiological properties of uniquely identifiable wild-type or mutant neurons can be assayed in behaving animals with the use of imaging techniques such as two-photon microscopy.

The MADM system also provides embodiments for studying other mammalian biological problems in vivo. For example, in stem cell biology the generation of single-colored cells is absolutely dependent on cell division. Hence, to study the elusive neural stem cells, the labeling ability of our MADM system is extremely useful for locating the origin of stem cells, identifying the progeny cell types, tracing their migration route and visualizing their functional neuronal connectivity. Another important application is to study tumor growth and metastasis. By knocking out tumor suppressor genes in an extremely limited number of cells, the MADM system reproduces the LOH (loss of heterozygosity) events that occur during tumor onset. The labeled homozygous mutant cells for tumor suppressor genes can be followed dynamically in vivo to study their abnormality and to assay the effects of therapeutic agents.

REFERENCES

1. Cajal, S. R., *Histology of the nervous system of man and vertebrates*. 1911, Oxford: Oxford University Press, Inc., 1995 translation.
2. Capecchi, M. R., *Altering the genome by homologous recombination*. Science, 1989. 244(4910): p. 1288-92.
3. Nagy, A., *Cre recombinase: the universal reagent for genome tailoring*. Genesis, 2000. 26(2): p. 99-109.
4. Lee, T. and L. Luo, *Mosaic analysis with a repressible cell marker (MARCM) for Drosophila neural development*. Trends Neurosci, 2001. 24(5): p. 251-4.
5. Lee, T. and L. Luo, *Mosaic analysis with a repressible cell marker for studies of gene function in neuronal morphogenesis*. Neuron, 1999. 22(3): p. 451-61.
6. Okada, A., et al., *Imaging cells in the developing nervous system with retrovirus expressing modified green fluorescent protein*. Exp Neurol, 1999. 156(2): p. 394-406.
7. Nakayama, A. Y., M. B. Harms, and L. Luo, *Small GTPases Rac and Rho in the maintenance of dendritic spines and branches in hippocampal pyramidal neurons*. J Neurosci, 2000. 20(14): p. 5329-38.
8. Soriano, P., *Generalized lacZ expression with the ROSA26 Cre reporter strain*. Nat Genet, 1999. 21(1): p. 70-1.
9. Zambrowicz, B. P., et al., *Disruption of overlapping transcripts in the ROSA beta geo 26 gene trap strain leads to widespread expression of beta-galactosidase in mouse embryos and hematopoietic cells*. Proc Natl Acad Sci USA, 1997. 94(8): p. 3789-94.
10. Lewandoski, M., E. N. Meyers, and G. R. Martin, *Analysis of Fgf8 gene function in vertebrate development*. Cold Spring Harb Symp Quant Biol, 1997. 62: p. 159-68.
11. Johnson, L., et al., *K-ras is an essential gene in the mouse with partial functional overlap with N-ras*. Genes Dev, 1997. 11(19): p. 2468-81.
12. Wojnowski, L., et al., *Craf-1 protein kinase is essential for mouse development*. Mech Dev, 1998. 76(1-2): p. 141-9.
13. Huang, E. J. and L. F. Reichardt, *Neurotrophins: roles in neuronal development and function*. Annu Rev Neurosci, 2001. 24: p. 677-736.
14. Finkbeiner, S. and M. E. Greenberg, *Ca (2+)-dependent routes to Ras: mechanisms for neuronal survival, differentiation, and plasticity?* Neuron, 1996. 16(2): p. 233-6.
15. Zou, Z., et al., *Genetic tracing reveals a stereotyped sensory map in the olfactory cortex*. Nature, 2001. 414 (6860): p. 173-9.
16. Jefferis, G. S., et al., *Target neuron prespecification in the olfactory map of Drosophila*. Nature, 2001. 414 (6860): p. 204-8.
17. Marin, E. C., et al., *Representation of the glomerular olfactory map in the Drosophila brain*. Cell, 2002. 109(2): p. 243-55.
18. Wong, A. M., J. W. Wang, and R. Axel, *Spatial representation of the glomerular map in the Drosophila protocerebrum*. Cell, 2002. 109(2): p. 229-41.
19. Hebert, J. M. and S. K. McConnell, *Targeting of cre to the Foxg1 (BF-1) locus mediates loxP recombination in the telencephalon and other developing head structures*. Dev Biol, 2000. 222(2): p. 296-306.
20. Smith, A. J., et al., *A site-directed chromosomal translocation induced in embryonic stem cells by Cre-loxP recombination*. Nat Genet, 1995. 9(4): p. 376-85.
21. Ramirez-Solis, R., P. Liu, and A. Bradley, *Chromosome engineering in mice*. Nature, 1995. 378(6558): p. 720-4.
22. Zheng, B., et al., *Engineering mouse chromosomes with Cre-loxP: range, efficiency, and somatic applications*. Mol Cell Biol, 2000. 20(2): p. 648-55.
23. Van Deursen, J., et al., *Cre-mediated site-specific translocation between nonhomologous mouse chromosomes*. Proc Natl Acad Sci USA, 1995. 92(16): p. 7376-80.
24. Liu, P., N. A. Jenkins, and N. G. Copeland, *Efficient Cre-loxP-induced mitotic recombination in mouse embryonic stem cells*. Nat Genet, 2002. 30(1): p. 66-72.
25. Koike, H., et al., *Efficient biallelic mutagenesis with Cre/loxP-mediated inter-chromosomal recombination*. EMBO Rep, 2002. 3(5): p. 433-7.

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A transgenic mouse whose genome comprises:
   (a) in a first chromosome of a chromosome pair, a first polynucleotide comprising a first promoter operably linked to a first chimeric sequence encoding an N-terminal portion of a first marker and a C-terminal portion of a second marker separated by a first target site of a recombinase; and
   (b) at a homologous location of a second chromosome of the chromosome pair, a second polynucleotide comprising a second promoter operably linked to a second chimeric sequence encoding an N-terminal portion of the second marker and a C-terminal portion of the first marker separated by a second target site of the recombinase, wherein presence of the recombinase promotes recombination between the target sites of the first and second chromosomes;
   wherein recombinase-promoted somatic mitotic recombination between the target sites yields alternative pairs of X- or Z-segregated progeny cells,
   wherein the X-segregated progeny cells comprise a first progeny cell comprising the first chromosome, and a recombined variant of the second chromosome comprising the second promoter operably linked to a sequence encoding the N- and C-terminal portions of the second marker; and a second progeny cell comprising the second chromosome, and a recombined variant of the first chromosome comprising the first promoter operably linked to a sequence encoding the N- and C-terminal portions of the first marker, and
   wherein the Z-segregated progeny cells comprise a first progeny cell comprising the first chromosome and the second chromosome, and a second progeny cell comprising a recombined variant of the first chromosome comprising the first promoter operably linked to a sequence encoding the N- and C-terminal portions of the first marker; and a recombined variant of the second chromosome comprising the second promoter operably linked to a sequence encoding the N- and C-terminal portions of the second marker,
   wherein the first X-segregated progeny cell produces a second marker-specific signal, the second X-segregated progeny cell produces a first marker marker-specific signal, the first Z-segregated progeny cell produces neither a first nor second marker-specific signal, and the second Z-segregated progeny cell produces both a first and a second marker specific-signal.

2. The mouse of claim 1, wherein the recombinase and target sites are selected from the group consisting of Cre/loxP and FLP/frt.

3. The mouse of claim 1, wherein the first and second markers are GFP and RFP.

4. The mouse of claim 2, wherein the recombinase and target sites are Cre/loxP, and the first and second markers are GFP and RFP.

5. The mouse of claim 1, wherein the first and second markers are transcriptional regulators.

6. The mouse of claim 1, wherein the somatic cell further comprises a genetic construct comprising a cell-type specific promoter operably linked to a sequence encoding the recombinase.

7. The mouse of claim 1, wherein the somatic cell further comprises a genetic construct comprising a drug-inducible promoter operably linked to a sequence encoding the recombinase, wherein the drug is selected from the group consisting of tamoxifen and doxycycline.

8. A transgenic mouse whose genome comprises:
   (a) in a first chromosome of a chromosome pair, a first polynucleotide comprising a first promoter operably linked to a first chimeric sequence encoding an N-terminal portion of a first fluorescent marker and a C-terminal portion of a second fluorescent marker separated by a first target site of a recombinase; and
   (b) at a homologous location of a second chromosome of the chromosome pair, a second polynucleotide comprising a second promoter operably linked to a second chimeric sequence encoding an N-terminal portion of the second marker and a C-terminal portion of the first marker separated by a second target site of the recombinase,
   wherein presence of the recombinase promotes recombination between the target sites of the first and second chromosomes;
   wherein recombinase-promoted somatic mitotic recombination between the target sites yields alternative pairs of X- or Z-segregated progeny cells,
   wherein the X-segregated progeny cells comprise a first progeny cell comprising the first chromosome, and a recombined variant of the second chromosome comprising the second promoter operably linked to a sequence encoding the N- and C-terminal portions of the second marker; and a second progeny cell comprising the second chromosome, and a recombined variant of the first chromosome comprising the first promoter operably linked to a sequence encoding the N- and C-terminal portions of the first marker, and
   wherein the Z-segregated progeny cells comprise a first progeny cell comprising the first chromosome and the second chromosome, and a second progeny cell comprising a recombined variant of the first chromosome comprising the first promoter operably linked to a sequence encoding the N- and C-terminal portions of the first marker; and a recombined variant of the second chromosome comprising the second promoter operably linked to a sequence encoding the N- and C-terminal portions of the second marker,
   wherein the first X-segregated progeny cell produces a second marker-specific fluorescent signal, the second X-segregated progeny cell produces a first marker-specific fluorescent signal, the first Z-segregated progeny cell produces neither a first nor second marker-specific fluorescent signal, and the second Z-segregated progeny cell produces both a first and a second marker-specific fluorescent signal.

9. A method to generate and mark chromosome recombination in somatic cells in a mouse, the method comprising:
   crossing a first transgenic mouse whose genome comprises a transgene comprising a promoter operably linked to a nucleic acid encoding a site-specific recombinase, with a second transgenic mouse that comprises in a first chromosome of a chromosome pair, a first polynucleotide comprising a first promoter operably linked to a first chimeric sequence encoding an N-terminal portion of a first marker and a C-terminal portion of a second marker separated by a first target site of the reconabinase, and at a homologous location of a second chromosome of the chromosome pair, a second polynucleotide comprising a second promoter operably linked to a second chimeric sequence encoding an N-terminal portion of the second marker and a C-terminal portion of the first marker separated by a second target site of the recombinase, to generate a progeny mouse that comprises the chromosome pair and expresses the recombinase, wherein expression of the recombinase promotes recombination between the target sites of the first and second chromosomes in somatic cells of the progeny mouse, wherein the recombinase-promoted somatic mitotic recombination between the target sites yields alternative pairs of X- or Z-segregated progeny cells, wherein the X-segregated progeny cells comprise a first progeny cell comprising the first chromosome, and a recombined variant of the second chromosome comprising the second promoter operably linked to a sequence encoding the N- and C-terminal portions of the second marker; and a second progeny cell comprising the second chromosome, and a recombined variant of the first chromosome comprising the first promoter operably linked to a sequence encoding the N- and C-terminal portions of the first marker, wherein the Z-segregated progeny cells comprise a first progeny cell comprising the first chromosome and the second chromosome, and a second progeny cell comprising a recombined variant of the first chromosome comprising the first promoter operably linked to a sequence encoding the N- and C-terminal portions of the first marker; and a recombined variant of the second chromosome comprising the second promoter operably linked to a sequence encoding the N- and C-terminal portions of the second marker, wherein the first X-segregated progeny cell produces a second marker-specific signal, the second X-segregated progeny cell produces a first marker-specific signal, the first Z-segregated progeny cell produces neither a first nor second marker-specific signal, and the second Z-segregated progeny cell produces both a first and a second marker specific-signal.

10. The method of claim 9, wherein the recombinase and target sites are Cre/loxP, and the first and second markers are GFP and RFP.

* * * * *